(12) United States Patent
Wilson et al.

(10) Patent No.: US 12,285,203 B2
(45) Date of Patent: *Apr. 29, 2025

(54) JAW FOR SURGICAL INSTRUMENT END EFFECTOR

(71) Applicant: Cilag GmbH International, Zug (CH)

(72) Inventors: James M. Wilson, Mason, OH (US); Randolph C. Stewart, Cincinnati, OH (US); Jason R. Lesko, Cincinnati, OH (US); Gregory A. Trees, Loveland, OH (US); Kristen L. D'Uva, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/539,517

(22) Filed: Dec. 14, 2023

(65) Prior Publication Data

US 2024/0108399 A1    Apr. 4, 2024

Related U.S. Application Data

(63) Continuation of application No. 16/931,495, filed on Jul. 17, 2020, now Pat. No. 11,857,247.

(51) Int. Cl.
*A61B 18/14* (2006.01)
*A61B 17/00* (2006.01)
(Continued)

(52) U.S. Cl.
CPC .............. *A61B 18/1445* (2013.01); *A61B 2017/00389* (2013.01); *A61B 2017/00734* (2013.01);
(Continued)

(58) Field of Classification Search
CPC ...... A61B 2017/00389; A61B 18/1445; A61B 2018/1455
See application file for complete search history.

(56) References Cited

U.S. PATENT DOCUMENTS 6,500,176 B1   12/2002   Truckai et al.
6,783,524 B2   8/2004    Anderson et al.
(Continued)

FOREIGN PATENT DOCUMENTS

WO    WO 2017/189413 A1   11/2017

OTHER PUBLICATIONS

International Search Report and Written Opinion dated Oct. 7, 2021, for International Application No. PCT/IB2021/056393, 14 pages.
(Continued)

*Primary Examiner* — Linda C Dvorak
*Assistant Examiner* — Ryan T Clark
(74) *Attorney, Agent, or Firm* — Frost Brown Todd LLP

(57) ABSTRACT

An apparatus including a body, a shaft assembly extending distally from the body, and an end effector configured to grasp and transmit RF energy to the tissue. The end effector includes a first jaw having a first tissue grasping feature and a second jaw. The second jaw is pivotably coupled to the first jaw between an open position, a partially closed position, and a closed position. The second jaw includes a proximal taper having a proximal electrode surface, a distal taper including a distal electrode surface, and a juncture between the proximal and distal electrode surface. The juncture is spaced further from the first tissue grasping feature compared to the proximal and distal end while the second jaw is in the partially closed position. The proximal and distal electrode surface deform to define a gap with the first tissue grasping feature while in the closed position.

20 Claims, 15 Drawing Sheets

(51) Int. Cl.
*A61B 17/29* (2006.01)
*A61B 18/00* (2006.01)
*A61B 18/12* (2006.01)

(52) U.S. Cl.
CPC ................ *A61B 2017/2925* (2013.01); *A61B 2018/00083* (2013.01); *A61B 2018/00601* (2013.01); *A61B 2018/0063* (2013.01); *A61B 2018/126* (2013.01); *A61B 2018/1455* (2013.01); *A61B 2018/1467* (2013.01)

(56) References Cited

U.S. PATENT DOCUMENTS

| | | |
|---|---|---|
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 8,461,744 B2 | 6/2013 | Wiener et al. |
| 8,888,809 B2 | 11/2014 | Davison et al. |
| 8,939,974 B2 | 1/2015 | Boudreaux et al. |
| 8,986,302 B2 | 3/2015 | Aldridge et al. |
| 9,089,327 B2 | 7/2015 | Worrell et al. |
| 9,161,803 B2 | 10/2015 | Yates et al. |
| 9,402,682 B2 | 8/2016 | Worrell et al. |
| 9,492,224 B2 | 11/2016 | Boudreaux et al. |
| 9,526,565 B2 | 12/2016 | Strobl |
| 9,545,253 B2 | 1/2017 | Worrell et al. |
| 9,877,720 B2 | 1/2018 | Worrell et al. |
| 10,292,758 B2 | 5/2019 | Boudreaux et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0015567 A1 | 1/2008 | Kimura |
| 2008/0200940 A1 | 8/2008 | Eichmann et al. |
| 2010/0058084 A1 | 3/2010 | Hanna |
| 2011/0184404 A1 | 7/2011 | Walberg et al. |
| 2011/0295314 A1* | 12/2011 | Staud .................... A61B 17/29 606/205 |
| 2014/0214025 A1* | 7/2014 | Worrell .............. A61B 18/1445 606/41 |
| 2017/0312018 A1 | 11/2017 | Trees et al. |
| 2017/0360500 A1 | 12/2017 | Rothweiler et al. |
| 2022/0015823 A1 | 1/2022 | Wilson et al. |

OTHER PUBLICATIONS

U.S. Appl. No. 61/410,603, Entitled "Energy-Based Surgical Instruments," filed Nov. 5, 2010.

* cited by examiner

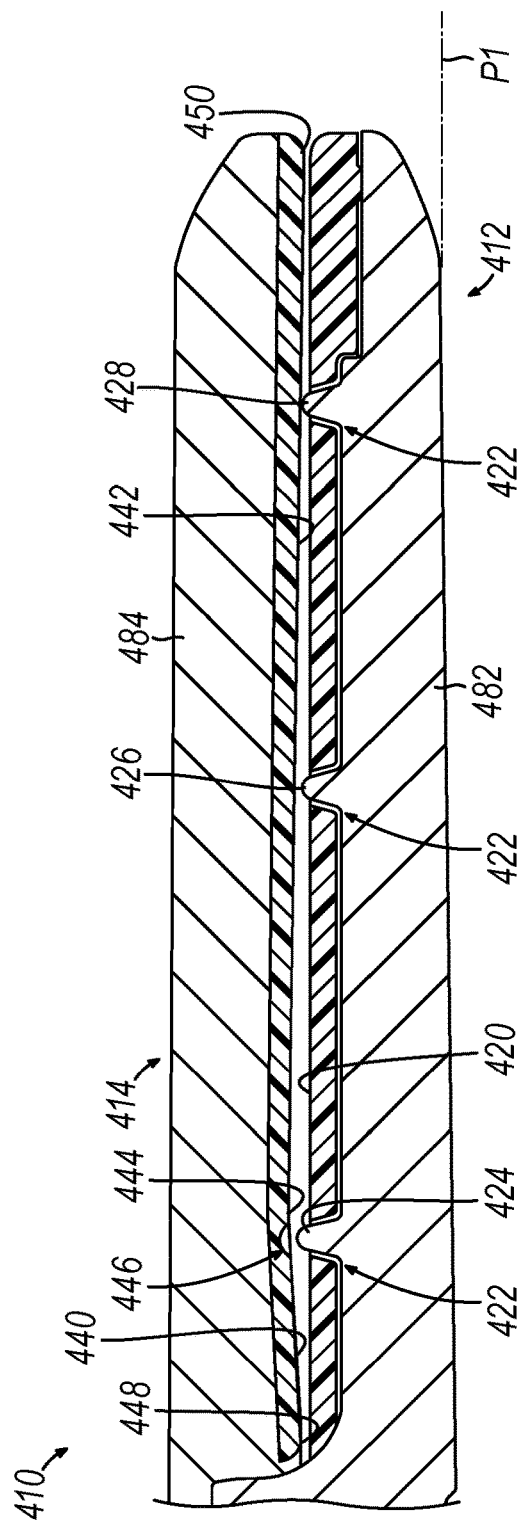
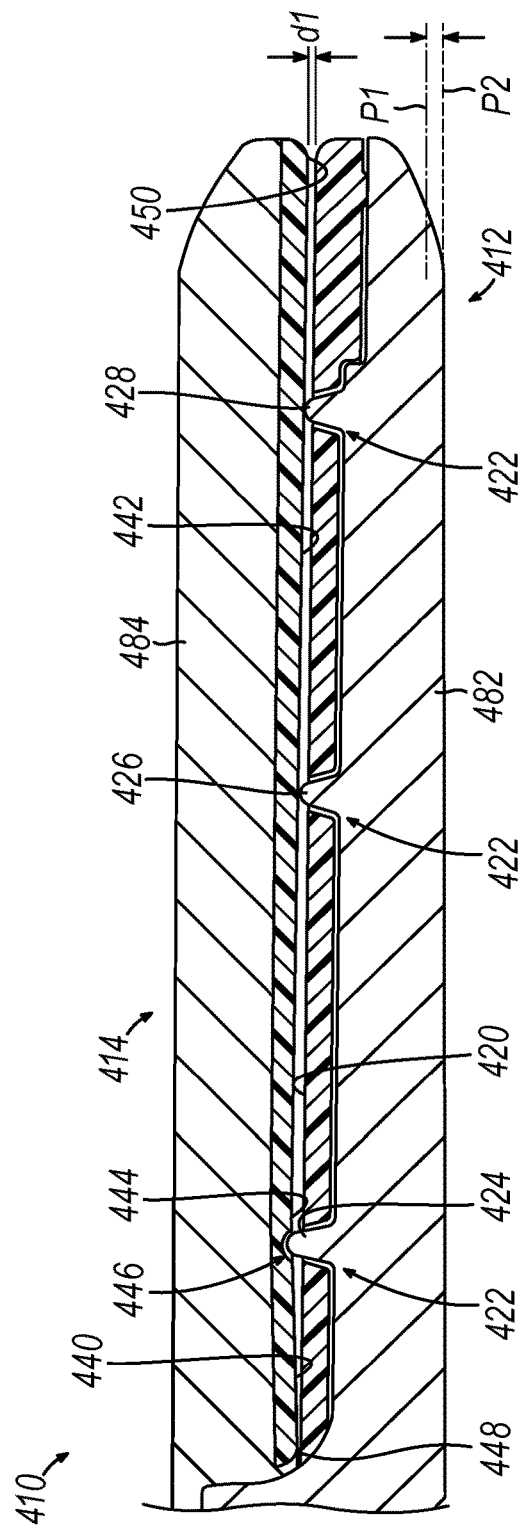
FIG. 9A
FIG. 9B

JAW FOR SURGICAL INSTRUMENT END EFFECTOR

PRIORITY

This application is a Continuation of U.S. patent application Ser. No. 16/931,495, entitled "Jaw For Surgical Instrument End Effector," filed on Jul. 17, 2020, issued as U.S. Pat. No. 11,857,247 on Jan. 2, 2024.

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 8,888,809, entitled "Surgical Instrument with Jaw Member," issued Nov. 18, 2014, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pat. No. 9,877,720, entitled "Control Features for Articulating Surgical Device," issued Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; and U.S. Pat. No. 9,545,253, entitled "Surgical Instrument with Contained Dual Helix Actuator Assembly," issued Jan. 17, 2017, the disclosure of which is incorporated by reference herein. Still other examples of electrosurgical cutting instruments and related concepts are disclosed in U.S. Pat. No. 9,526,565, entitled "Electrosurgical Devices," issued Dec. 27, 2016, the disclosure of which is incorporated by reference herein; U.S. Pat. No. 9,492,224, entitled "Multi-Function Bi-Polar Forceps," issued Nov. 15, 2016, the disclosure of which is incorporated by reference herein; and U.S. Pat. No. 10,292,758, entitled "Methods and Devices for Articulating Laparoscopic Energy Device," issued May 21, 2019, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9A depicts a cross-sectional side view of the end effector of FIG. 4 in the partially closed state;

FIG. 9B depicts a cross-sectional side view of the end effector of FIG. 4 in the completely closed state;

Figure 1:
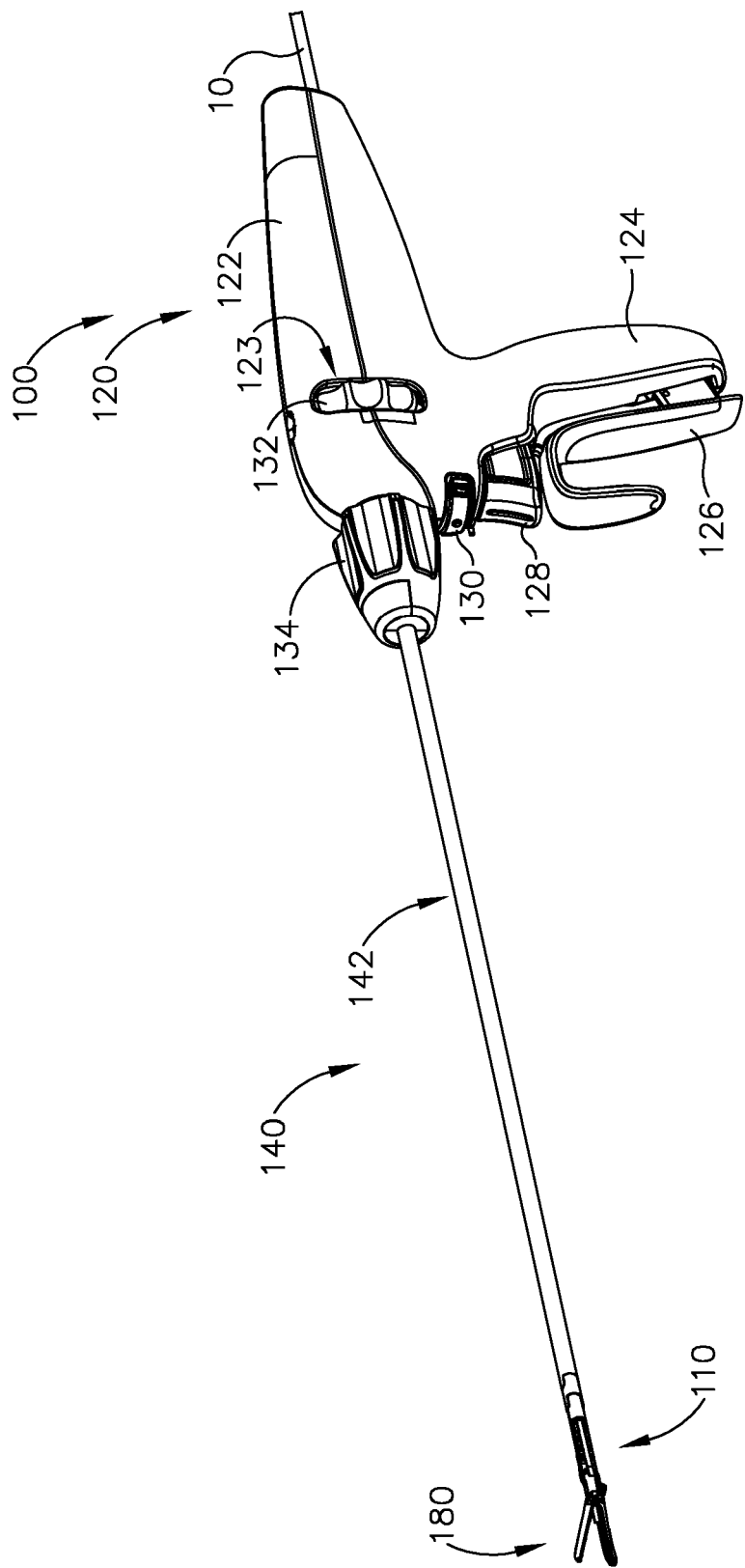
FIG. 1 depicts a perspective view of an exemplary electrosurgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Instrument

FIGS. 1-3C show an exemplary electrosurgical instrument (100). As best seen in FIG. 1, electrosurgical instrument (100) includes a handle assembly (120), a shaft assembly (140), an articulation assembly (110), and an end effector (180). As will be described in greater detail below, end effector (180) of electrosurgical instrument (100) is operable to grasp, cut, and seal or weld tissue (e.g., a blood vessel, etc.). In this example, end effector (180) is configured to seal or weld tissue by applying bipolar radio frequency (RF) energy to tissue. However, it should be understood electrosurgical instrument (100) may be configured to seal or weld tissue through any other suitable means that would be apparent to one skilled in the art in view of the teachings herein. For example, electrosurgical instrument (100) may be configured to seal or weld tissue via an ultrasonic blade, staples, etc. In the present example, electrosurgical instrument (100) is electrically coupled to a power source (not shown) via power cable (10).

The power source may be configured to provide all or some of the electrical power requirements for use of electrosurgical instrument (100). Any suitable power source may be used as would be apparent to one skilled in the art in view of the teachings herein. By way of example only, the power source may comprise a GEN04 or GEN11 sold by Ethicon Endo-Surgery, Inc. of Cincinnati, Ohio. In addition, or in the alternative, the power source may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. While in the current example, electrosurgical instrument (100) is coupled to a power source via power cable (10), electrosurgical instrument (100) may contain an internal power source or plurality of power sources, such as a battery and/or supercapacitors, to electrically power electrosurgical instrument (100). Of course, any suitable combination of power sources may be utilized to power electrosurgical instrument (100) as would be apparent to one skilled in the art in view of the teaching herein.

Handle assembly (120) is configured to be grasped by an operator with one hand, such that an operator may control and manipulate electrosurgical instrument (100) with a single hand. Shaft assembly (140) extends distally from handle assembly (120) and connects to articulation assembly (110). Articulation assembly (110) is also connected to a proximal end of end effector (180). As will be described in greater detail below, components of handle assembly (120) are configured to control end effector (180) such that an operator may grasp, cut, and seal or weld tissue. As will also be described in greater detail below, articulation assembly (110) is configured to deflect end effector (180) from the longitudinal axis defined by shaft assembly (140).

Handle assembly (120) includes a body (122), a pistol grip (124), a jaw closure trigger (126), a knife trigger (128), an activation button (130), an articulation control (132), and a knob (134). As will be described in greater detail below, jaw closure trigger (126) may be pivoted toward and away from pistol grip (124) and/or body (122) to open and close jaws (182, 184) of end effector (180) to grasp tissue. Additionally, knife trigger (128) may be pivoted toward and away from pistol grip (124) and/or body (122) to actuate a knife member (360) within the confines of jaws (182, 184) to cut tissue captured between jaws (182, 184). Further, activation button (130) may be pressed to apply radio frequency (RF) energy to tissue via electrode surfaces (194, 196) of jaws (182, 184), respectively.

Body (122) of handle assembly (120) defines an opening (123) in which a portion of articulation control (132) protrudes from. Articulation control (132) is rotatably disposed within body (122) such that an operator may rotate the portion of articulation control (132) protruding from opening (123) to rotate the portion of articulation control (132) located within body (122). Rotation of articulation control (132) relative to body (122) is configured to bend articulation section (110) in order to drive deflection of end effector (180) from the longitudinal axis defined by shaft assembly (140). Articulation control (132) and articulation section (110) may include any suitable features to drive deflection of end effector (180) from the longitudinal axis defined by shaft assembly (140) as would be apparent to one skilled in the art in view of the teachings herein.

Knob (134) is rotatably disposed on the distal end of body (122) and configured to rotate end effector (180), articulation assembly (110), and shaft assembly (140) about the longitudinal axis of shaft assembly (140) relative to handle assembly (120). While in the current example, end effector (180), articulation assembly (110), and shaft assembly (140)

are rotated by knob (134), knob (134) may be configured to rotate end effector (180) and articulation assembly (110) relative to selected portions of shaft assembly (140). Knob (134) may include any suitable features to rotate end effector (180), articulation assembly (110), and shaft assembly (140) as would be apparent to one skilled in the art in view of the teachings herein.

Shaft assembly (140) includes distal portion (142) extending distally from handle assembly (120), and a proximal portion (not shown) housed within the confines of body (122) of handle assembly (120). Shaft assembly (140) houses a jaw closure connector (338) that couples jaw closure trigger (126) with end effector (180). Additionally, shaft assembly (140) houses an actuating member that couples knife member (360) with knife trigger (128). Shaft assembly (140) also houses actuating members that couple articulation assembly (110) with articulation control (132); as well as an electrical connecter that operatively couples electrode surfaces (194, 196) with activation button (130). As will be described in greater detail below, jaw closure connector (338) is configured to translate relative to shaft assembly (140) to open and close jaws (182, 184) of end effector (180); while knife member (360) is coupled to knife trigger (128) of handle assembly (120) to translate a distal cutting edge (362) within the confines of end effector (180); and activation button (130) is configured to activate electrode surface (194, 196).

Figure 2:
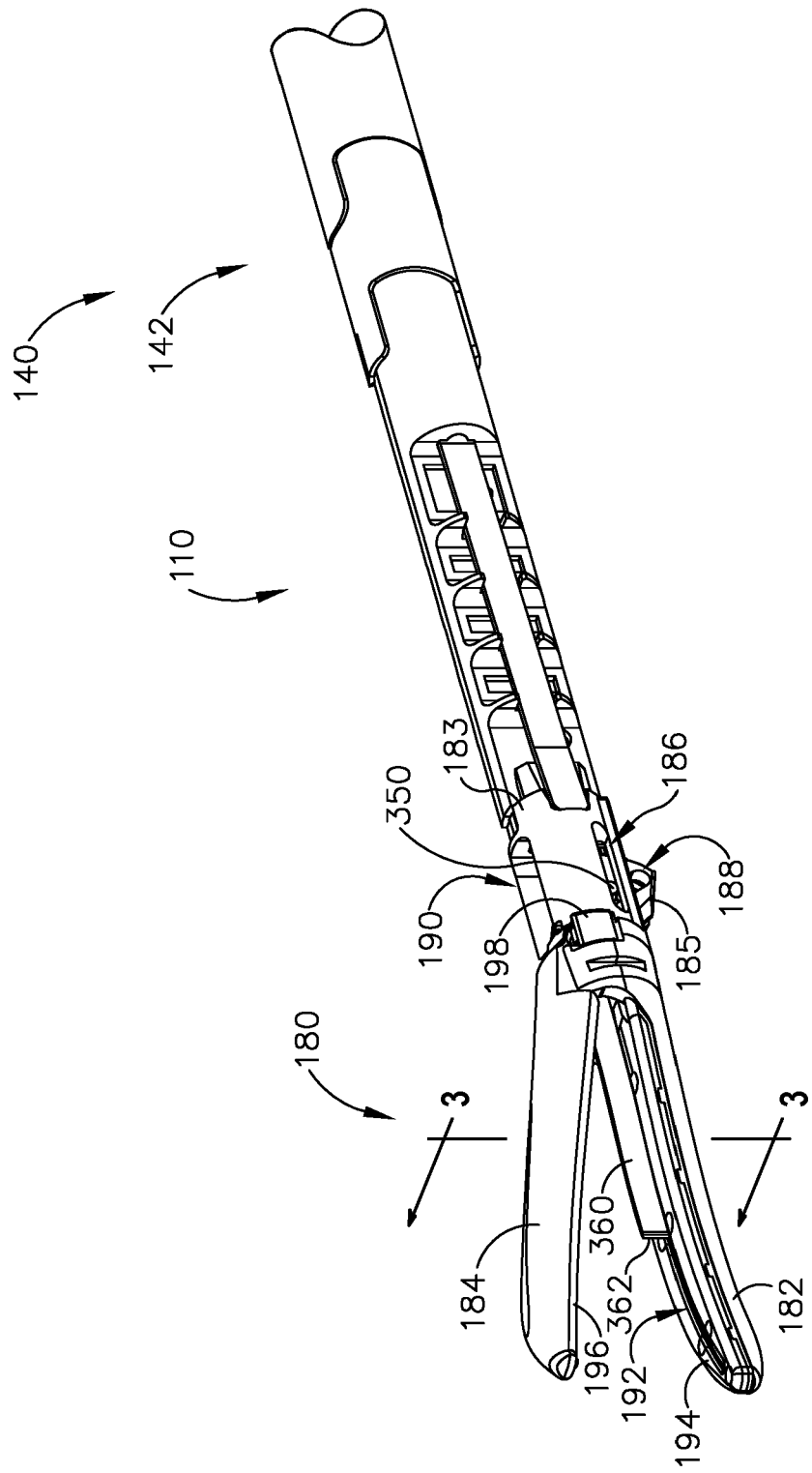
FIG. 2 depicts a perspective view of an exemplary articulation assembly and end effector of the electrosurgical instrument of FIG. 1.
Figure 3A:
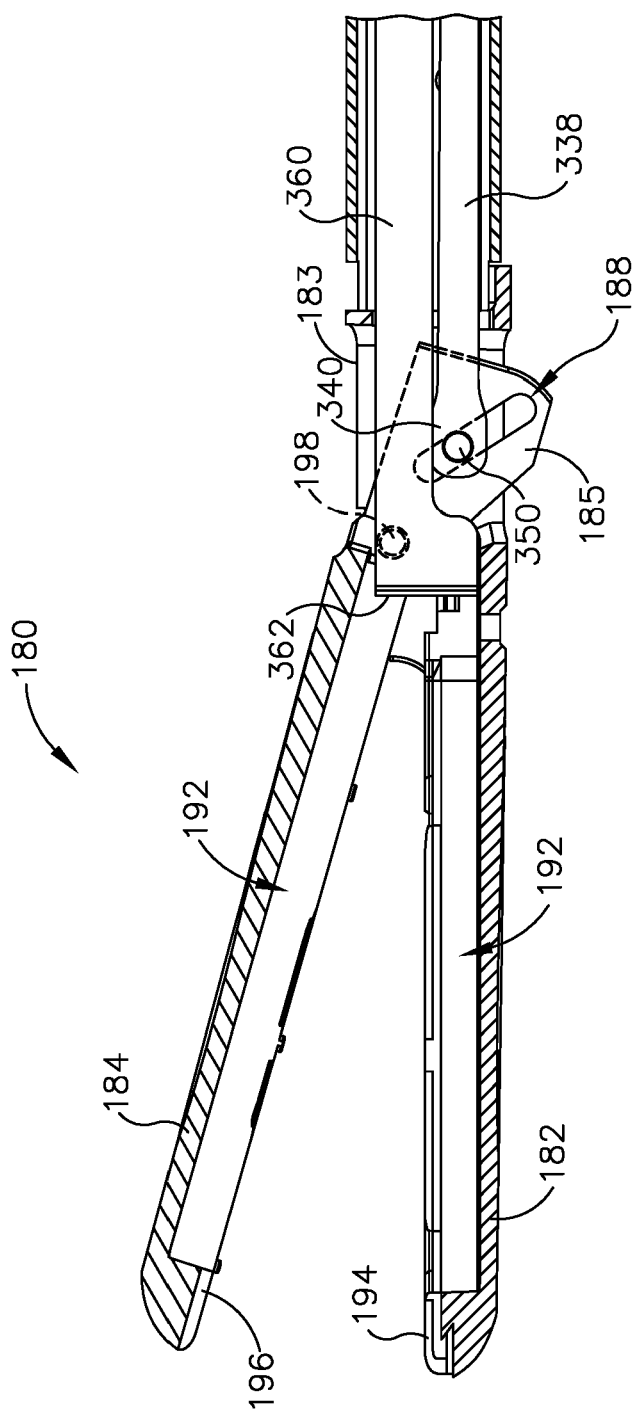
FIG. 3A depicts a cross-sectional side view of the end effector of FIG. 2, where the end effector is in the open and unfired state, taken along line 3-3 of FIG. 2.
Figure 3B:
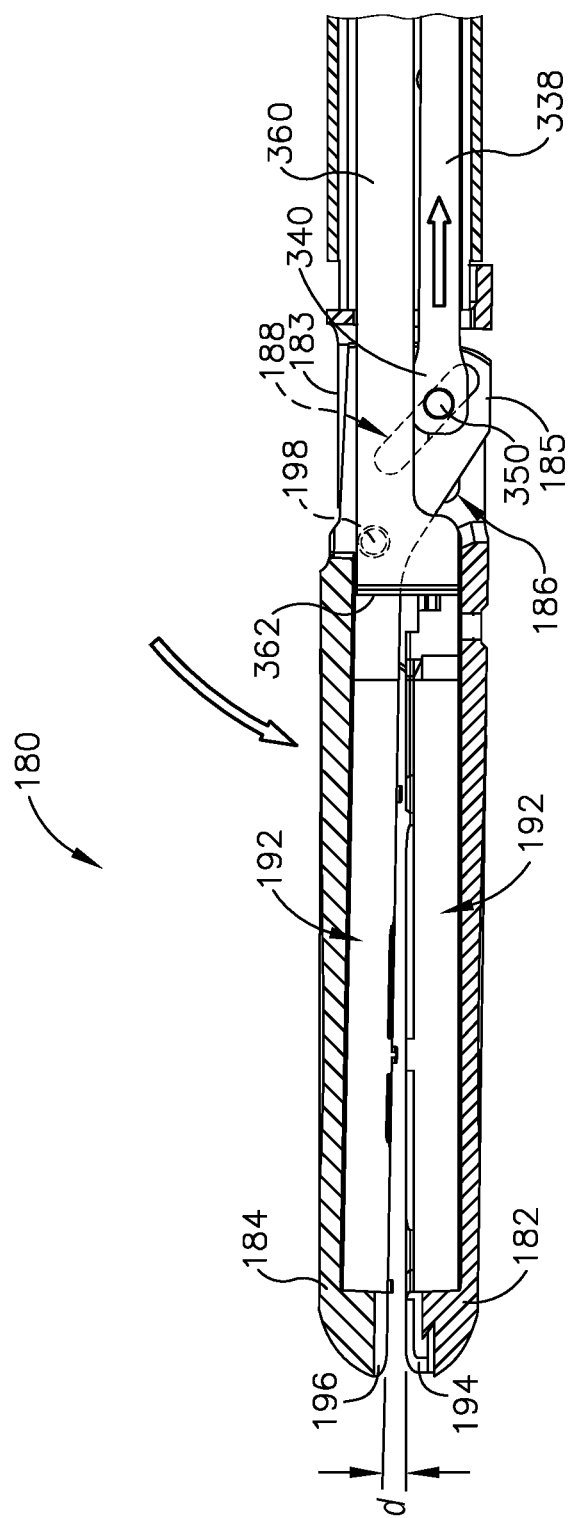
FIG. 3B depicts a cross-sectional side view of the end effector of FIG. 2, where the end effector is in the closed and unfired state, taken along line 3-3 of FIG. 2.
Figure 3C:
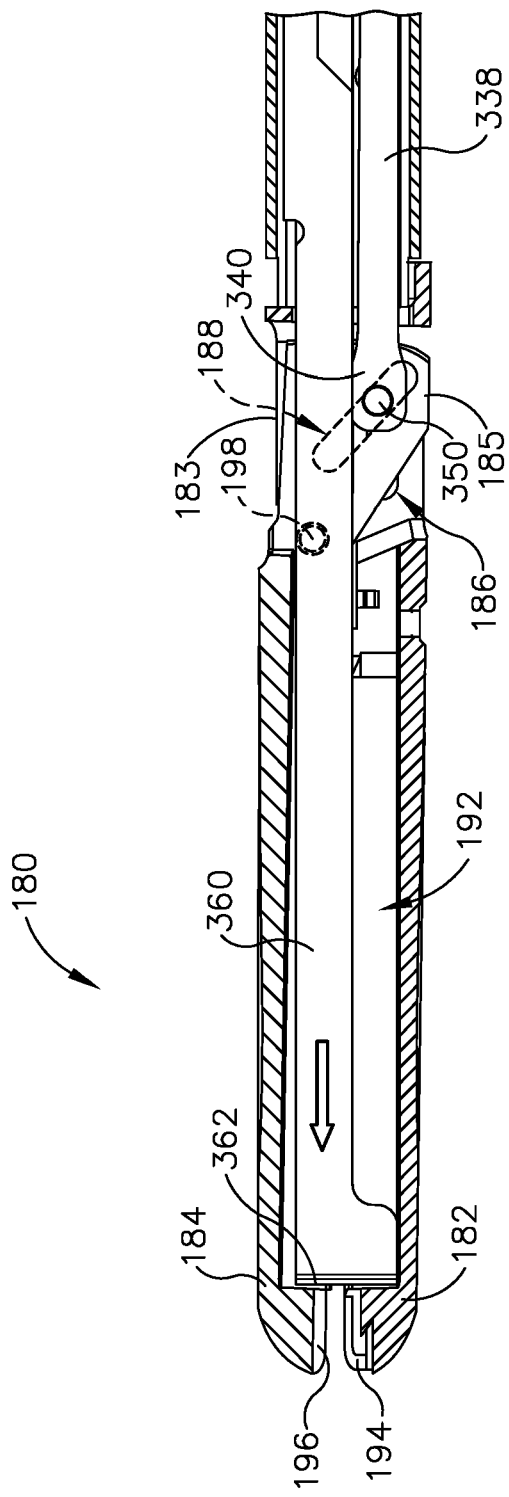
FIG. 3C depicts a cross-sectional side view of the end effector of FIG. 2, where the end effector is in the closed and fired state, taken along line 3-3 of FIG. 2.

As best seen in FIGS. 2-3C, end effector (180) includes lower jaw (182) pivotally coupled with an upper jaw (184) via pivot couplings (198). Lower jaw (182) includes a proximal body (183) defining a slot (186), while upper jaw (184) includes proximal arms (185) defining a slot (188). Lower jaw (182) also defines a central channel (190) that is configured to receive proximal arms (185) of upper jaw (184), portions of knife member (360), jaw closure connecter (338), and pin (350). Slots (186, 188) each slidably receive pin (350), which is attached to a distal coupling portion (340) of jaw closure connector (338). As will be described in greater detail below, jaw closure connector (338) is operable to translate within central channel (190) of lower jaw (182). Translation of jaw closure connector (330) drives pin (350). As will be described in greater detail below, because pin (350) is located within both slots (186, 188) and slots (186, 188) are angled relative to each other, pin (350) cams against proximal arms (185) to pivot upper jaw (184) toward and away from lower jaw (182) about pivot couplings (198). Therefore, upper jaw (184) is configured to pivot toward and away from lower jaw (182) about pivot couplings (198) to grasp tissue.

The term "pivot" does not necessarily require rotation about a fixed axis, but may include rotation about an axis that moves relative to end effector (180). Therefore, the axis at which upper jaw (184) pivots about lower jaw (182) may translate relative to both upper jaw (184) and lower jaw (182). Any suitable translation of the pivot axis may be used as would be apparent to one skilled in the art in view of the teachings herein.

Lower jaw (182) and upper jaw (184) also define a knife pathway (192). Knife pathway (192) is configured to slidably receive knife member (360), such that knife member (360) may be retracted (as shown in FIGS. 3A-3B), and advanced (as shown in FIG. 3C), to cut tissue captured between jaws (182, 184). Lower jaw (182) and upper jaw (184) each comprise a respective electrode surface (194, 196). The power source may provide RF energy to electrode surfaces (194, 196) via electrical coupling that extends through handle assembly (120), shaft assembly (140), articulation assembly (110), and electrically couples with one or both of electrode surfaces (194, 196). Electrical coupling may selectively activate electrode surfaces (194, 196) in response to an operator pressing activation button (130).

FIGS. 3A-3C show an exemplary use of instrument (100) for end effector (180) to grasp, cut, and seal/weld tissue. Jaw closure trigger (126) may be pivoted toward and away from pistol grip (124) and/or body (122) to open and close jaws (182, 184) of end effector (180) to grasp tissue. In particular, pivoting jaw closure trigger (126) toward pistol grip (124) may proximally actuate jaw closure connector (338) and pin (350), which in turn cams against slots (188) of proximal arms (185) of upper jaw (184), thereby rotating upper jaw (184) about pivot couplings (198) toward lower jaw (182) such that jaws (182, 184) achieve a closed configuration. If the operator desires to open jaws (182, 184), the operator may pivot jaw closure trigger (126) away from pistol grip (124), such that pin (350) actuates distally to drive upper jaw (184) away from lower jaw (182). In some instances, jaw closure trigger (126) is biased toward the open position such that upper jaw (184) is biased to the open configuration. Any suitable features that cause pivoting of jaw closure trigger (126) to actuate pin (350) may be used as would be apparent to one skilled in the art in view of the teachings herein.

Next, as shown between FIGS. 3B-3C, knife trigger (128) may be pivoted toward and away from body (122) and/or pistol grip (124) to actuate knife member (360) within knife pathway (192) of jaws (182, 184) to cut tissue captured between jaws (182, 184). Any suitable features may be used in order to actuates knife member (360) as would be apparent to one skilled in the art in view of the teachings herein. In some instances, knife trigger (128) may be biased to the position associated with knife member (360) in a retracted position.

With distal cutting edge (362) of knife member (360) actuated to the advance position (position shown in FIG. 8C), an operator may press activation button (130) to selectively activate electrode surfaces (194, 196) of jaws (182, 184) to weld/seal severed tissue that is captured between jaws (182, 184). It should be understood that the operator may also press activation button (130) to selectively activate electrode surfaces (194, 196) of jaws (182, 184) at any suitable time during exemplary use. Therefore, the operator may also press activation button (130) while knife member (360) is retracted as shown in FIGS. 3A-3B. Next, the operator may release jaw closure trigger (128) such that jaws (182, 184) pivot into the opened configuration, releasing tissue.

II. Exemplary Alternative End Effector for Electrosurgical Instrument

As mentioned above, end effector (180) is configured to grasp, sever, and weld/seal tissue. In particular, jaw (184) may pivot relative to jaw (182) in order to grasp tissue, while knife member (360) is configured to actuate within jaws (182, 184) in order to sever grasped tissue. Electrode surfaces (194, 196) may be activated while jaws (182, 184) grasp tissue in order to weld/seal tissue captured between jaws (182, 184).

While welding/sealing tissue captured between jaws (182, 184), an appropriate gap distance (d) between electrode surfaces (194, 196) may be desirable along the entire length of electrode surfaces (194, 196). If adjacent portions of electrode surfaces (194, 196) that cooperatively grasp tissue form a gap distance (d) (as best shown in FIG. 3B) that is too small, tissue grasped between electrode surfaces (194, 196)

may become damaged, crushed, etc. Additionally, if gap distance (d) is too small, electrode surfaces (194, 196) may come into incidental contact with each other to cause an undesirable short circuit. Conversely, if adjacent portions of electrode surfaces (194, 196) that cooperatively grasp tissue form a gap distance (d) that is too large, electrode surfaces (194, 196) may not properly weld/seal tissue grasped between electrode surfaces (194, 196).

In some instances, the gap distance (d) between electrode surfaces (194, 196) may deviate along the length of electrode surfaces (194, 196) such that a proximal portion of electrode surfaces (194, 196) form a gap distance (d) of a first size, and a distal portion of electrode surfaces (194, 196) form a gap distance (d) of a second size. Therefore, in some instances, due at least in part to the deviation in gap distance (d), a first longitudinal portion of electrode surface (194, 196) may create an acceptable tissue seal/weld, while a second longitudinal portion of electrode surfaces (194, 196) may have too large or too small a gap distance that may cause undesirable effects as mention above. It may therefore be desirable to provide a form of end effector (180) that reliably provides a gap distance (d) that achieves the desired effects, while avoiding undesired effects, along the entire length of the tissue contacting region of the end effector. An example of such a form of end effector (180) is described in greater detail below.

FIGS. 4 and 8A-9B show an exemplary end effector (480) that may be readily incorporated into electrosurgical instrument (100) in replacement of end effector (180) described above. End effector (480) is substantially similar to end effector (180) described above, with differences elaborated below. As will be described in greater detail below, end effector (480) includes a tissue grasping assembly (410) that is configured to form an appropriate non-uniform gap distance (d1) along the length of tissue grasping portions (412, 414) in order to promote an acceptable weld/seal of grasped tissue in accordance with the description herein.

End effector (480) includes a lower jaw (482), an upper jaw (484), a proximal body (483) extending proximally from lower jaw (482), and a pair of proximal arms (485) extending proximally from upper jaw (483). Lower jaw (482), upper jaw (484), proximal body (483), and proximally extending arms (485) may be substantially similar to lower jaw (182), upper jaw (184), proximal body (183), and proximal arms (185) described above, with difference elaborated below.

Therefore, proximal body (183) defines a central channel (490) and a slot (486), while proximal arms (485) define a slot (488), which are substantially similar to central channel (190), slot (186), and slot (188) described above, respectively. Additionally, lower jaw (482) and upper jaw (484) are pivotably coupled via pivot couplings (498), which may be substantially similar to pivot couplings (198) described above. Therefore, lower jaw (482) and upper jaw (484) are configured to pivot relative to each other about pivot couplings (498) in order to grasp tissue via translation of pin (350) within slots (186, 188). Additionally, lower jaw (482) and upper jaw (484) define a knife pathway (492) dimensioned to slidably receive knife member (360) in accordance with the description herein.

As mentioned above, end effector (480) also includes tissue grasping assembly (410). Tissue grasping assembly (410) includes lower tissue grasping portion (412) associated with lower jaw (482) and upper tissue grasping (414) portion associated with upper jaw (484).

Figure 4:
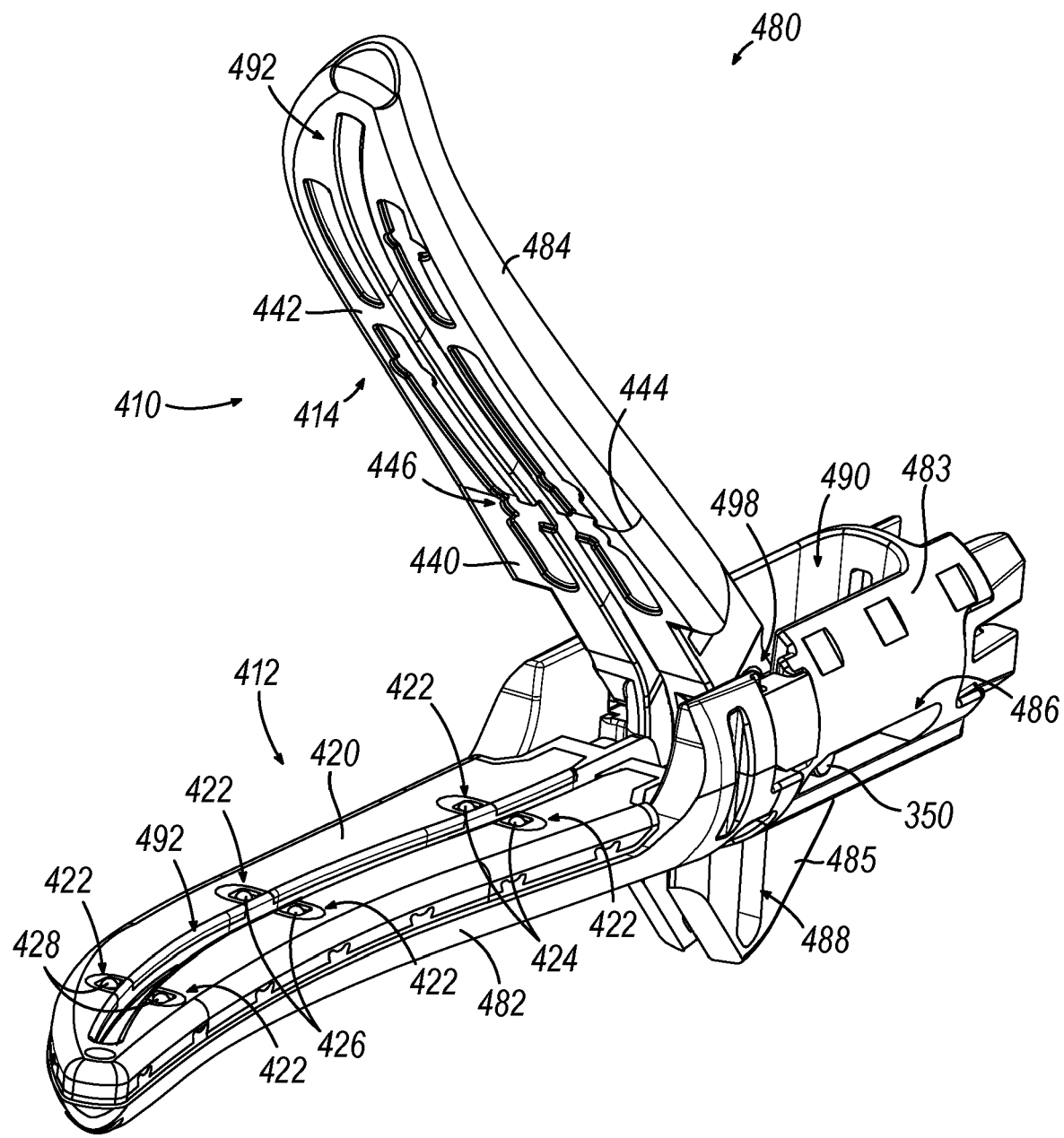
FIG. 4 depicts a perspective view of an alternative exemplary end effector.
Figure 5:
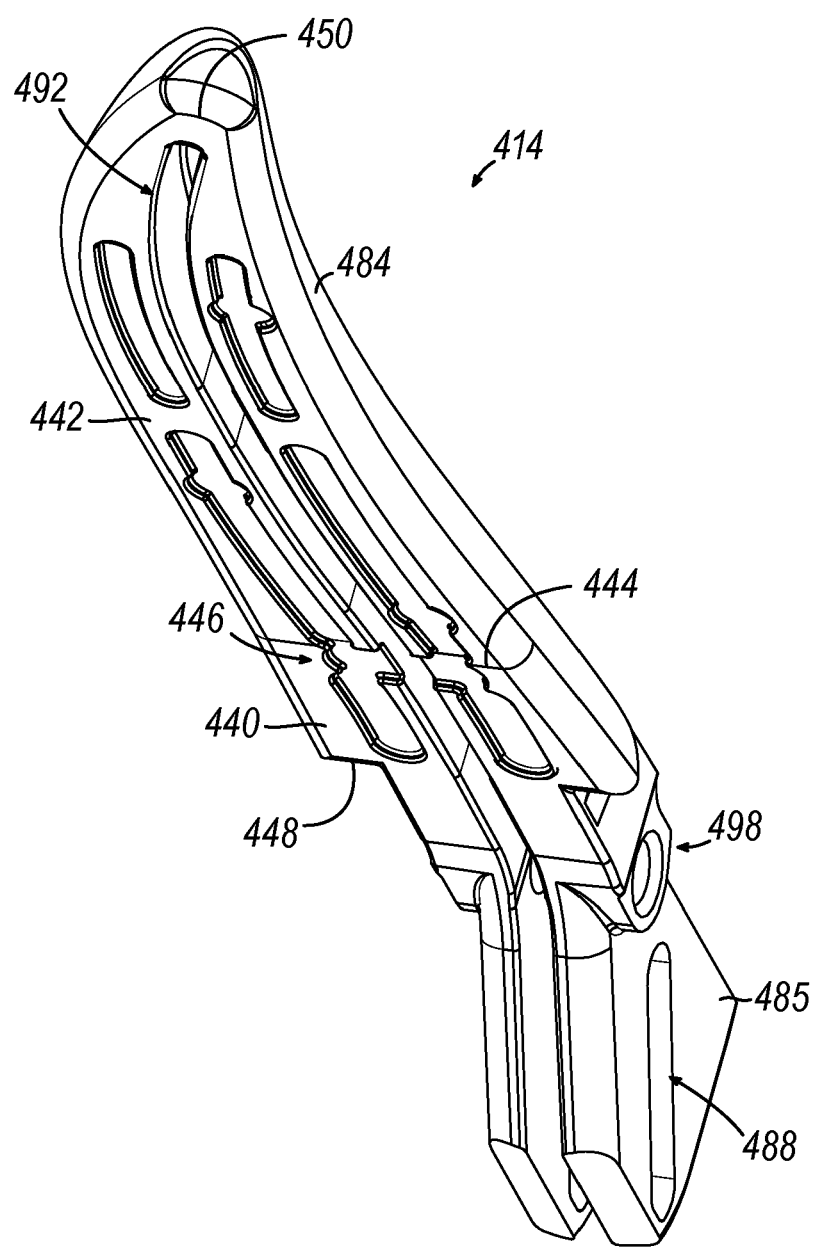
FIG. 5 depicts a perspective view of an upper jaw of the end effector of FIG. 4.
Figure 6:
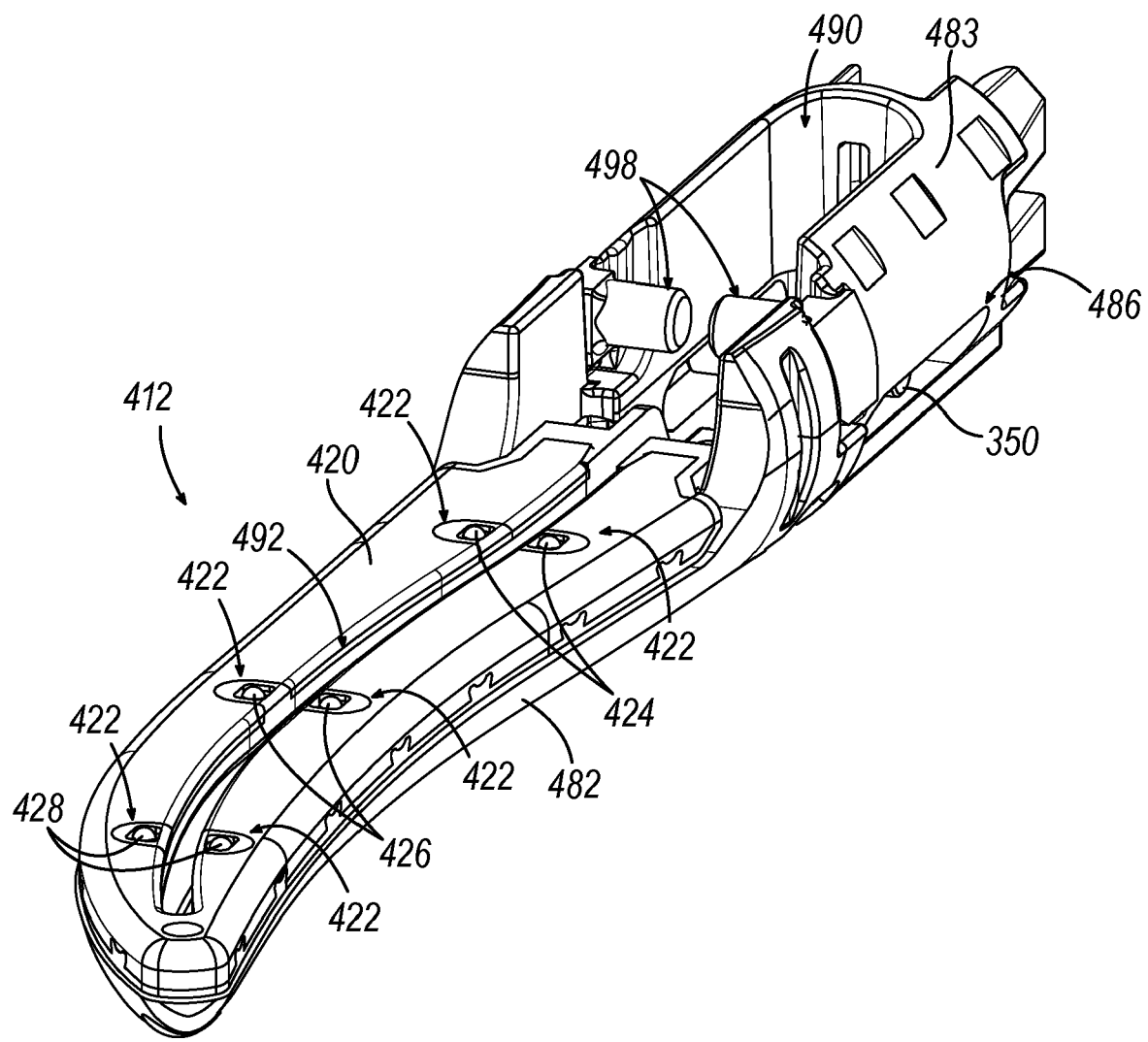
FIG. 6 depicts a perspective view of a lower jaw of the end effector of FIG. 4.

As best shown in FIGS. 4 and 6, lower tissue grasping portion (412) includes an electrode surface (420) defining a plurality of pockets (422). Similar to electrode surface (194) described above, electrode surface (420) may be suitably coupled with a power source such that the power source may provide RF energy to electrode surface (420) via an electrical coupling. Therefore, the operator may selectively activate electrode surface (420) by pressing activation button (130) in accordance with the description above.

Electrode surface (420) may be coupled to lower jaw (482) through any suitable means as would be apparent to one skilled in the art in view of the teachings herein. For example, electrode surface (420) may be coupled to lower jaw (484) via an adhesive, welding, an interference fit, a snap fitting, a latch, a dovetail joint, etc.

Lower tissue grasping portion (412) also includes a pair of proximal teeth (424), a pair of middle teeth (426), and a pair of distal teeth (428). Each tooth (424, 426, 428) is housed within a respective pocket (422) defined by electrode surface (420). Teeth (424, 426, 428) are electrically insulated from electrode surface (420) while also extending above the electrode surface (420). Therefore, if any tooth (424, 426, 428) comes into contact with electrode surfaces (440, 442) of upper jaw tissue grasping portion (414), a short circuit may be prevented.

Figure 8A:
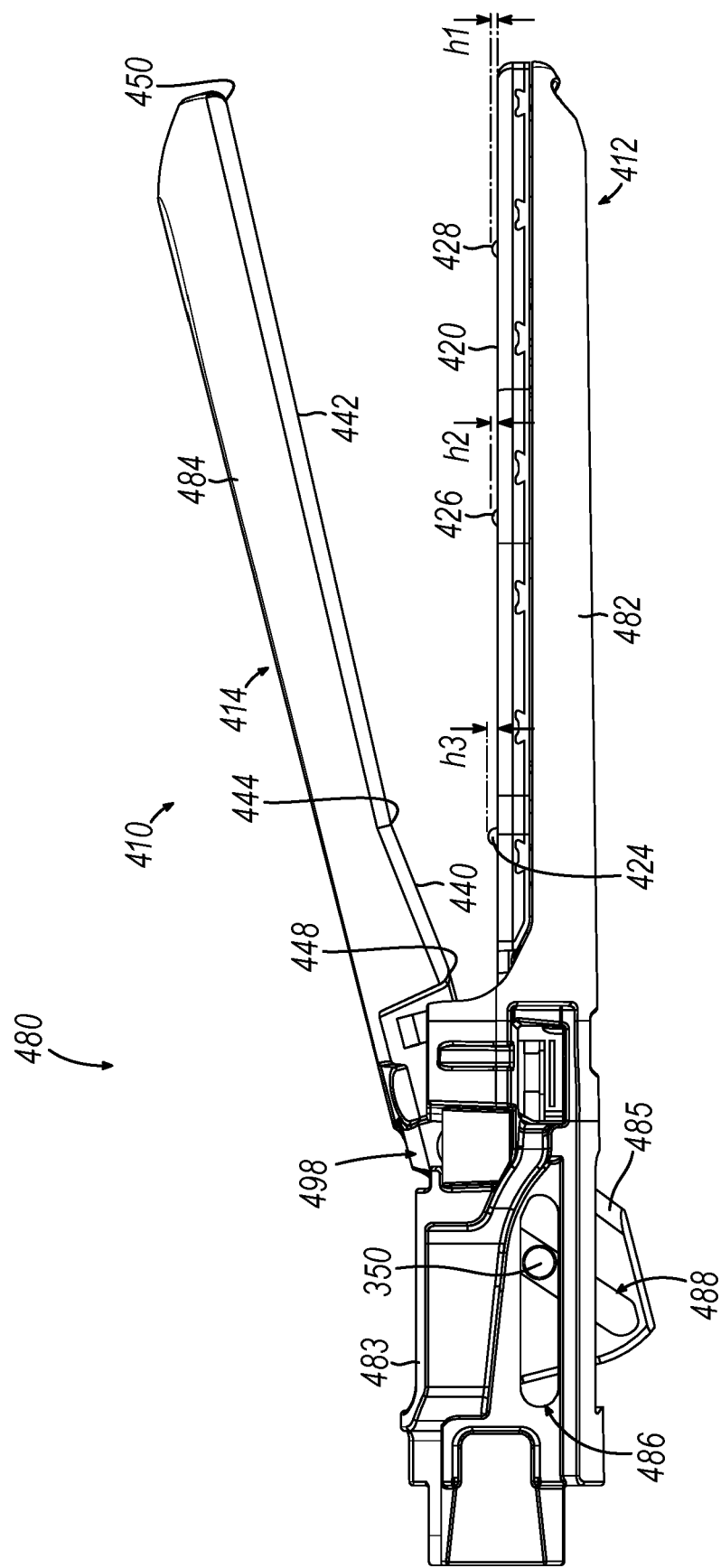
FIG. 8A depicts an elevation side view of the end effector of FIG. 4 in an open state.

In the current example, teeth (424, 426, 428) have different heights relative to electrode surface (420). In particular, as shown in FIG. 8A, distal teeth (428) extend to a first height (h1) above electrode surface (420); meddle teeth (426) extend to a second height (h2) above electrode surface (420); and proximal teeth (424) extend to a third height (h3) above electrode surface (420). In the present example, second height (h2) is greater than first height (h1); and third height (h3) is greater than second height (h2). Thus, teeth (428, 426, 428) progressively increase in height in the direction from the distal end of lower jaw (482) toward the proximal end of lower jaw (482). In some other versions, progressively decrease in height from the distal end of lower jaw (482) toward the proximal end of lower jaw (482), such that second height (h2) is less than first height (h1); and third height (h3) is less than second height (h2). In still other versions, teeth (428, 426, 428) are all at the same height relative to electrode surface (420). (424, 426, 428) may extend any suitable distance away from electrode surface (420) as would be apparent to one skilled in the art in view of the teachings herein.

As will be described in greater detail below, distal teeth (428) and middle teeth (426) are configured to abut against distal tapered electrode surface (442) in order to impart a reactionary force to upper tissue grasping portion (414) as upper jaw (484) is pivoted into a completely closed configuration. The reactionary force imparted on upper tissue grasping portion (414), along with the compliant nature and geometry of upper tissue grasping portion (414), may induce a sufficient bending moment so electrode surfaces (440, 442) and electrode surface (420) form an appropriate non-uniform gap distance (dl) between adjacent portions of electrode surface (420) and corresponding electrode surface (440, 442). This appropriate gap distance (d1) may extend between a proximal end (448) and a distal end (450) of upper tissue grasping portion (414), though the gap distance (d1) may still slightly vary along the length extending between proximal end (448) and distal end (450).

While in the current example, there are three sets of teeth (424, 426, 428) longitudinally spaced apart from each other, any suitable number of teeth (424, 426, 428) in any suitable array/pattern may be used as would be apparent to one skilled in the art in view of the teachings herein.

Figure 7:
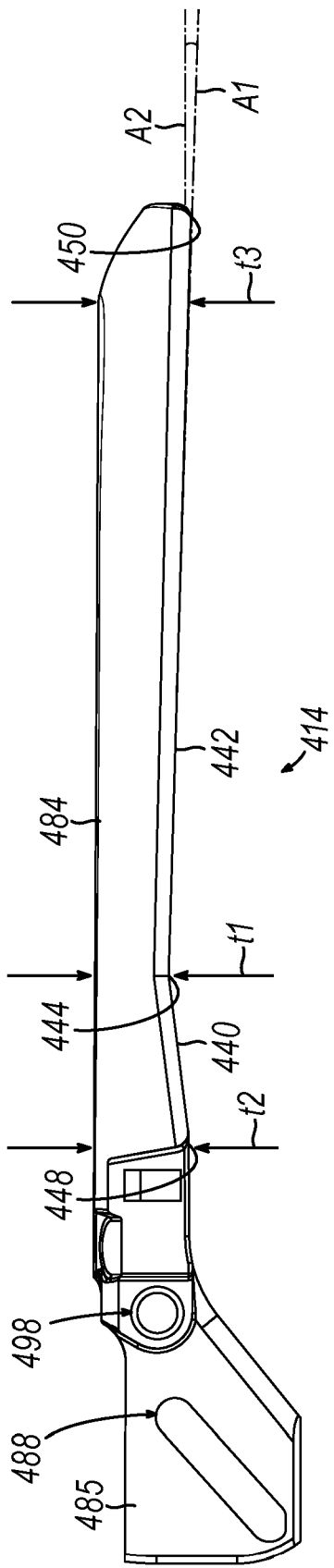
FIG. 7 depicts an elevation side view of the upper jaw of FIG. 5.

As best shown in FIGS. 4 and 7, upper tissue grasping portion (414) includes a proximal tapered electrode surface (440) and a distal tapered electrode surface (442) meeting at a juncture (444), such that upper jaw (484) is cambered. In some variations, lower jaw (482) may be cambered similar to how upper jaw (484) is cambered as described herein; in addition to upper jaw (484) being cambered as described herein. In still other variations, lower jaw (482) may be cambered similar to how upper jaw (484) is cambered as described herein; while upper jaw (484) is non-cambered. In the present example, similar to electrode surface (196) described above, electrode surfaces (440, 442) may be suitably coupled with the power source such that the power source may provide RF energy to electrode surfaces (440, 442) via an electrical coupling. Therefore, the operator may selectively activate electrode surfaces (440, 442) by pressing activation button (130) in accordance with the description above. It should be understood that electrode surface (420) may cooperate with electrode surfaces (440, 442) to apply bipolar RF energy to tissue that is captured between electrode surface (420) and electrode surfaces (440, 442).

Proximal tapered electrode surface (440) extends from a proximal end (448) to juncture (444) while distal tapered electrode surface (442) extends from juncture (444) to distal end (450). In particular, proximal tapered electrode surface (440) extends upwardly, as viewed from the perspective shown in FIG. 7, from proximal end (448) to juncture (444); while distal tapered electrode surface (442) extends downwardly, as viewed from the perspective shown in FIG. 7, from juncture (444) to distal end (450).

Proximal tapered electrode surface (440) and distal tapered electrode surface (442) may be in electrical communication with each other. Additionally, proximal tapered electrode surface (440) and distal tapered electrode surface (442) may be unitarily formed as a single piece of material, may be formed with the same material, may be formed from two separate pieces of material, may be formed from different material, etc. A suitable portion of either one or both of electrode surface (440, 442) defines a recess (446) dimensioned to align with proximal teeth (424) of lower tissue grasping portion (412) when jaws (482, 484) are in the fully closed configuration, as will be described in greater detail below. Recess (446) is suitably sized such that when jaws (482, 484) are in the fully closed configuration, proximal teeth (424) do not contact electrode surfaces (440, 442).

Figure 8B:
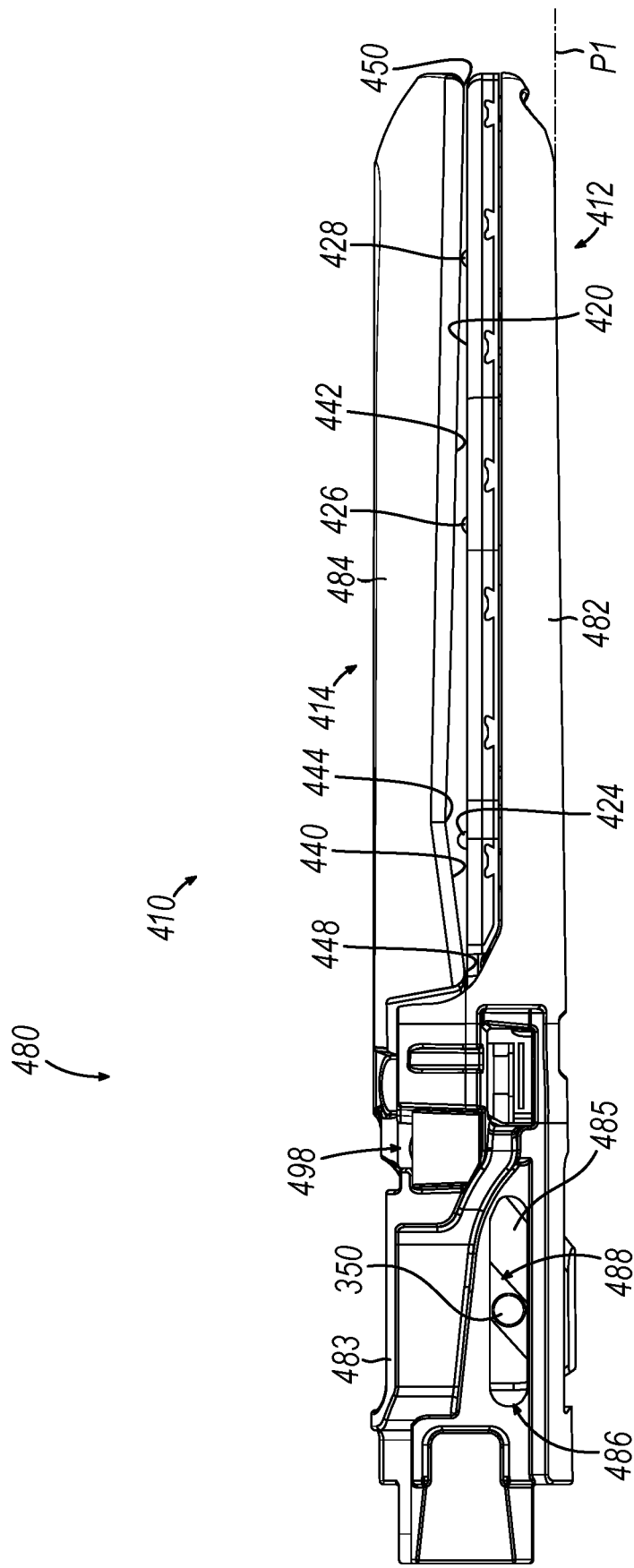
FIG. 8B depicts an elevation side view of the end effector of FIG. 4 in a partially closed state.

Proximal tapered electrode surface (440) and distal tapered electrode surface (442) are coupled with upper jaw (484) forming a general double taper such that when upper jaw (484) is pivoted to a position that initially makes contact with lower jaw (482), as shown in FIGS. 8B and 9A, the portions of tapered electrode surfaces (440, 442) forming juncture (444) is furthest away from electrode surface (420) of lower jaw (482) compared to the portions of tapered electrode surfaces (440, 442) at proximal end (448) and distal end (450), respectively. Juncture (444) may be located along any suitable longitudinal portion of upper jaw (484) as would be apparent to one skilled in the art in view of the teachings herein. Therefore, tapered electrode surface (440, 442) may have any suitable length, length ratio, etc., as would be apparent to one skilled in the art in view of the teachings herein. While in the current example, juncture (444) extends linearly and perpendicular between lateral sides of electrode surfaces (440, 442), this is merely optional. Juncture (444) may laterally extends across electrode surfaces (440, 442) having any suitable geometry as would be apparent to one skilled in the art in view of the teachings herein.

The general double taper formed by electrode surfaces (440, 442) extending from juncture (444) to respective ends (448, 450) may have any suitable angle relative to electrode surface (420) as would be apparent to one skilled in the art in view of the teachings herein. In the current example, the angles formed by tapered electrode surfaces (440, 442) are exaggerated for purposes of clarity.

Additionally, any suitable geometry of tapered electrode surfaces (440, 442) may be used as would be apparent to one skilled in the art in view of teachings herein. For example, electrode surfaces (440, 442) may have a substantially planar profile and generally rectangular perimeter. As another example, electrode surfaces (440, 442) may extend from juncture (444) to respective ends (448, 450) along a slightly arched profile, in either a slightly convex or concave, with a rounded, smooth, perimeter.

As exemplified in FIG. 7, distal electrode surface (442) may extend along an axis (A2) that defines an angle with a datum axis (A1) extending parallel to the longitudinal axis defined by shaft assembly (140). Similarly, proximal electrode surface (440) may also extend along an axis that defines another angle with datum axis (A1). The angles formed by tapered electrode surfaces (440, 442) and datum axis (A1) may be formed through any suitably manner as would be apparent to one skilled in the art in view of the teaching herein.

As best shown in FIG. 7, the double taper formed in the current example is formed by a change in thickness of electrode surface (440, 442) and corresponding portions of upper jaw (484) such that the thickness (t1) at juncture (444) is smaller than the thickness (t2) at proximal end (448) and the thickness (t3) at distal end (550). The changes in thickness forming double taper may be changes in thickness to upper jaw (484) alone, changes in thickness of electrode surfaces (440, 442) alone, or a combination of both.

Tapered electrode surfaces (440, 442) may be coupled to upper jaw (484) through any suitable means as would be apparent to one skilled in the art in view of the teachings herein. For example, tapered electrode surface (440, 442) may be coupled to upper jaw (484) via an adhesive, welding, an interference fit, a snap fitting, a latch, a dovetail joint, etc.

Electrode surfaces (440, 442), as well as any other suitable components of upper tissue grasping portion (414) and upper jaw (484), may be suitably compliable, elastically deformable, resilient, etc., to deform in response to a suitable bending moment. It should be understood that electrode surfaces (420, 440, 442) may be formed from any suitable material as would be apparent to one skilled in the art in view of the teachings herein.

As will be described in greater detail below, electrode surfaces (440, 442) are suitably elastically deformable, such that electrode surfaces (440, 442) form an appropriate non-uniform gap distance (d1) when upper jaw (484) is pivoted from an initially closed position into a fully closed position.

FIGS. 8A-9B show an exemplary use of end effector (480) in accordance with the description herein. FIG. 8A shows end effector (480) in an open position such that lower tissue grasping portion (412) and upper tissue grasping portion (414) are configured to accept tissue between both portions (412, 414). While end effector (480) is in the open position, tapered electrode surfaces (440, 442) form the double taper as described above.

Next, as shown in FIGS. 8B and 9A, the operator may pivot upper jaw (484) toward lower jaw (482) by pulling closure trigger (126) to proximally translate pin (350) in accordance with the description herein. In particular, the operator may pivot upper jaw (484) toward lower jaw (482)

until distal tapered electrode surface (442) initially contacts distal teeth (428). At the position shown in FIGS. 8B and 9A, proximal tapered electrode surface (440) is not parallel with electrode surface (420); and distal tapered electrode surface (442) is not parallel with electrode surface (420). Also at the position shown in FIGS. 8B and 9A, contact between distal tapered electrode surface (442) and distal teeth (428) does not impart a sufficient reactionary force on upper jaw (484) and tapered electrode surfaces (440, 442) to induce a sufficient bending moment on electrode surfaces (440, 442). Therefore, tapered electrode surfaces (440, 442) maintain their initial geometry such that junction (444) is further away from an adjacent portion of electrode surface (420) as compared to proximal end (448) and distal end (450) of respective tapered electrode surfaces (440, 442). Therefore, at the position shown in FIGS. 8B and 9A, the gap distance between tapered electrode surfaces (440, 442) and electrode surface (420) is not substantially uniform along the length of tissue grasping portions (412, 414).

Figure 10:
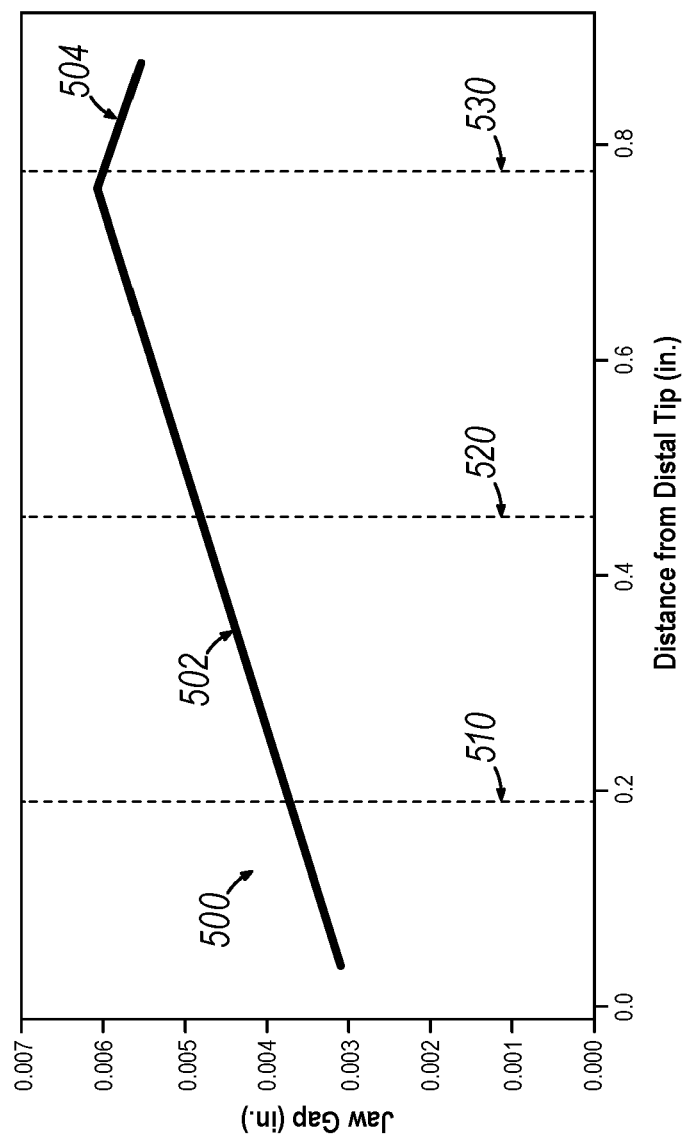
FIG. 10 depicts a graph plotting a gap between jaws of the end effector of FIG. 4 in the partially closed state.

To further illustrate the non-parallel relationship between electrode surfaces (440, 442) and electrode surface (420) at the state shown in FIGS. 8B and 9A, FIG. 10 depicts a plot (500) showing an example of a gap distance between electrode surfaces (440, 442) and electrode surface (420) as a function of the distance from distal end (450) of upper tissue grasping portion (414). It should be understood that the numerical values shown in FIG. 10 are merely illustrative examples and are not intended to be limiting in any way. In FIG. 10, a first segment (502) of plot (500) corresponds to the gap distance between distal tapered electrode surface (440) and lower electrode surface (420); while a second segment (504) of plot (500) corresponds to the gap distance between proximal tapered electrode surface (440) and lower electrode surface (420). Also in FIG. 10, a first broken vertical line (510) corresponds to the longitudinal position of distal tooth (428), a second broken vertical line (520) corresponds to the longitudinal position of middle tooth (426), and a third broken vertical line (530) corresponds to the longitudinal position of proximal tooth (424).

Figure 8C:
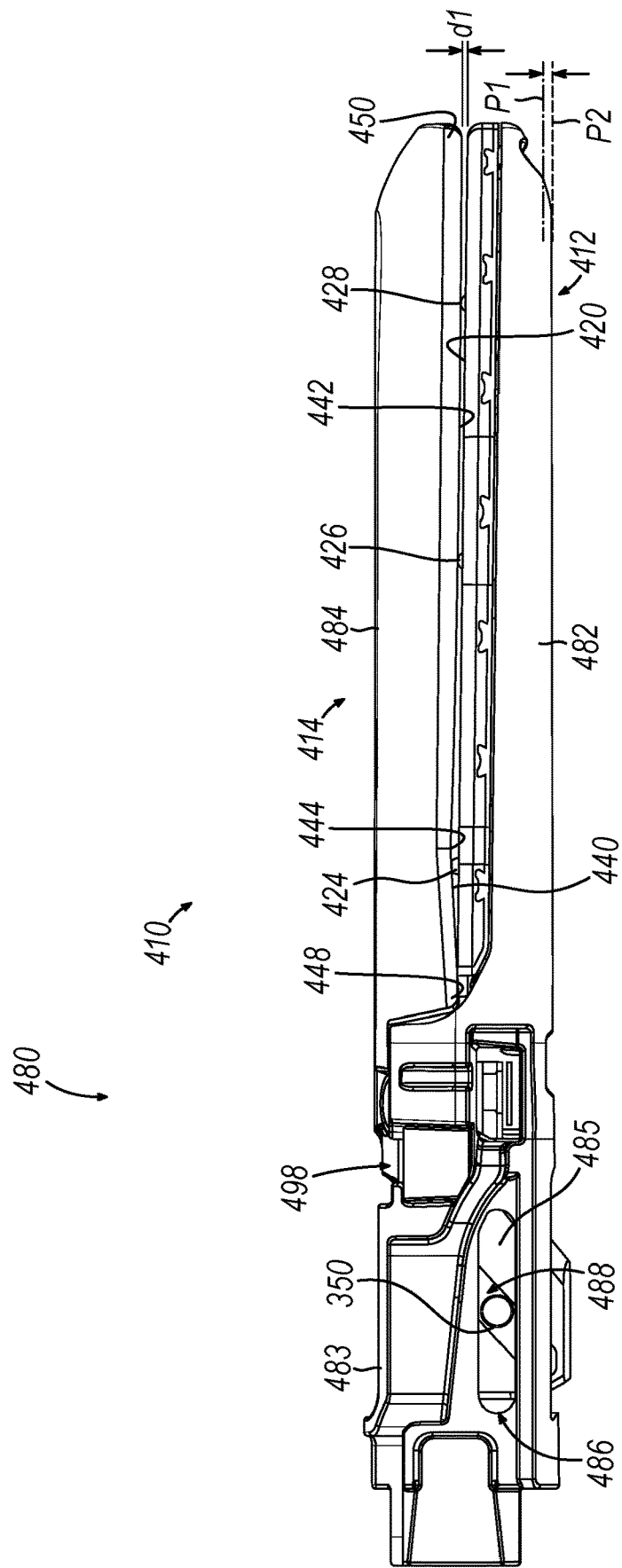
FIG. 8C depicts an elevation side view of the end effector of FIG. 4 in a completely closed state.

Next, as shown in FIGS. 8C and 9B, the operator may further pivot upper jaw (484) toward lower jaw (482) by further pulling closure trigger (126) to further proximally translate pin (350) in accordance with the description herein until closure trigger (126) is latched and/or pivoted to its completely closed position. Further proximal translation of pin (350) may impart a sufficient reactionary force on upper jaw (484) and tapered electrode surfaces (440, 442) from contact with distal teeth (428) to induce a sufficient bending moment on electrode surfaces (440, 442).

The induced bending moment may cause distal tapered electrode (442) to contact middle teeth (426) so middle teeth (426) also impart a reactionary force on upper jaw (484) and tapered electrode surfaces (440, 442). The portion of distal tapered electrode surface (442) located distal to middle teeth (426) may define a portion of gap distance (d1) with adjacent portions of electrode surface (420) through contact with middle teeth (426) and distal teeth (428). Additionally, the bending moment generated by further proximal translation of pin (350) may bend/elastically deform the portion of distal tapered electrode surface (442) located proximal to middle teeth (426), juncture (444), and proximal tapered electrode (442) closer to adjacent portions of electrode surface (420) to also define a portion of gap distance (d1). Therefore, gap distance (d1) may extend between a proximal end (448) and a distal end (450) of upper tissue grasping portion (414). However, in the present example, gap distance (d1) is not uniform along the entire length extending between proximal end (448) and distal end (450), even in the state shown in FIGS. 8C and 9B. In other words, even in the state shown in FIGS. 8C and 9B, proximal tapered electrode surface (440) is still not parallel with electrode surface (420); and distal tapered electrode surface (442) is still not parallel with electrode surface (420). Nevertheless, the distance between juncture (444) and electrode surface (420) in the state shown in FIGS. 8C and 9B is still smaller than the distance between juncture (444) and electrode surface (420) in the state shown in FIGS. 8B and 9A. In some other variations, gap distance (d1) may be uniform along the length of electrode surfaces (420, 440, 442) in the state shown in FIGS. 8C and 9B, such that electrode surfaces (440, 442) may be parallel with electrode surface (420) in the state shown in FIGS. 8C and 9B.

Figure 11:
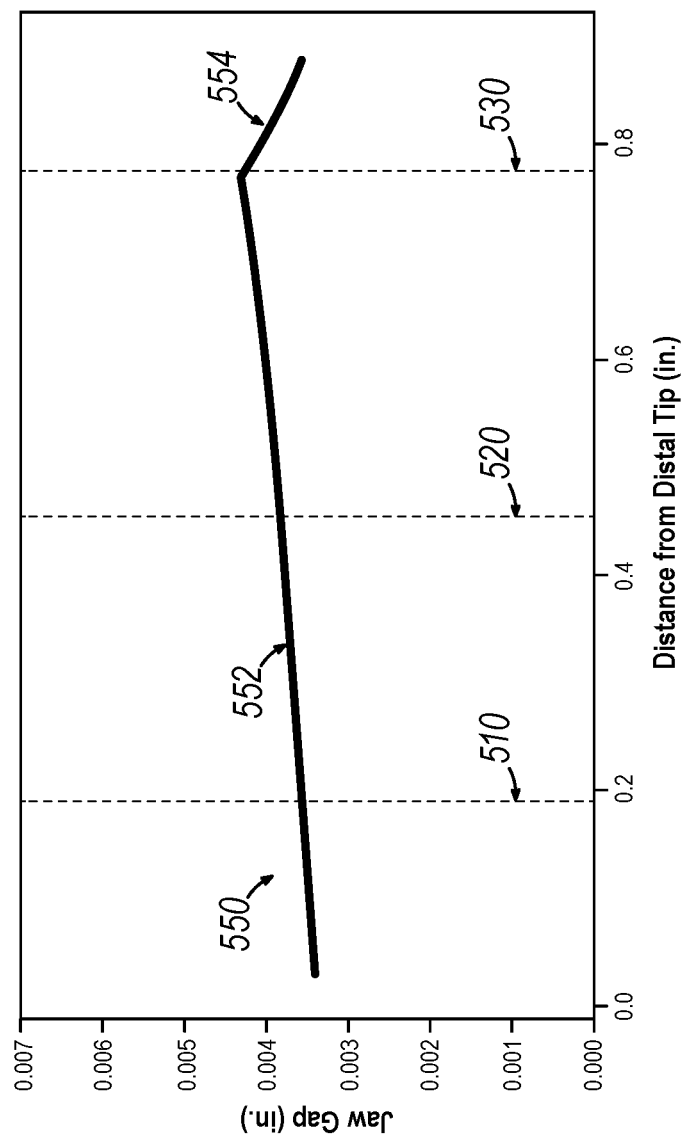
FIG. 11 depicts a graph plotting a gap between jaws of the end effector of FIG. 4 in the completely closed state.

To further illustrate the non-parallel relationship between electrode surfaces (440, 442) and electrode surface (420) at the state shown in FIGS. 8C and 9B, FIG. 11 depicts a plot (550) showing an example of a gap distance between electrode surfaces (440, 442) and electrode surface (420) as a function of the distance from distal end (450) of upper tissue grasping portion (414). FIG. 11 may be regarded as being drawn to scale with respect to some versions of end effector (480). It should be understood that the numerical values shown in FIG. 11 are merely illustrative examples and are not intended to be limiting in any way. In FIG. 11, a first segment (552) of plot (550) corresponds to the gap distance between distal tapered electrode surface (440) and lower electrode surface (420); while a second segment (554) of plot (550) corresponds to the gap distance between proximal tapered electrode surface (440) and lower electrode surface (420). Also in FIG. 11, broken vertical lines (510, 520, 530) corresponds to the longitudinal position of teeth (428, 426, 424) in the same manner as found in FIG. 10.

By way of further example only, at the state shown in FIGS. 8C and 9B, FIG. 11, the gap distance between proximal end (448) of upper tissue grasping portion (414) and lower electrode surface (420) may range from approximately 0.001 inches to approximately 0.006 inches By way of further example only, at the state shown in FIGS. 8C and 9B, FIG. 11, the gap distance between juncture (444) of upper tissue grasping portion (414) and lower electrode surface (420) may range from approximately 0.001 inches to approximately 0.006 inches By way of further example only, at the state shown in FIGS. 8C and 9B, FIG. 11, the gap distance between distal end (450) of upper tissue grasping portion (414) and lower electrode surface (420) may range from approximately 0.001 inches to approximately 0.006 inches The foregoing gap value ranges are merely illustrative examples and are not intended to be limiting in any way.

By way of further example only, the gap distance between upper electrode surfaces (440, 442) and lower electrode surface (420) may vary along the length of electrode surfaces (420, 440, 442) (i.e., the length between proximal end (448) and distal end (450), including juncture (444)), from the largest gap distance to the smallest gap distance, by a percentage range from approximately 10% to approximately 80%, with the largest gap distance being at juncture (444). The foregoing gap change percentage range is a merely illustrative example and is not intended to be limiting in any way.

In some scenarios, contact generated between distal tapered electrode surface (442) and teeth (426, 428) may also be sufficient to slightly deform lower jaw (482) from a first vertical position (p1) to a second, lowered vertical position (p2). Deformation of lower jaw (482) may also help achieve a desirable yet non-uniform final gap distance (d1).

As best seen in FIG. 9B, proximal teeth (424) are housed within recess (446) of electrode surfaces (440, 442) when final gap distance (d1) is formed such that proximal teeth (424) do not contact any surface of recess (446) or either electrode surface (440, 442). Therefore, proximal teeth (424) may not impart another reactionary force on upper jaw (484) and tapered electrode surface (440, 442) in the present example. The absence of reactionary force generated by contact with proximal teeth (424) and electrode surface (440, 442) may help assure the bending moment within electrode surfaces (440, 442) is sufficient to elastically deform electrode surfaces (440, 442) to sufficiently define the appropriate, non-uniform final gap distance (d1) along the entire length of electrode surfaces (440, 442).

With an appropriate, non-uniform final gap distance (d1) created, the operator may activate electrode surface (420, 440, 442) in accordance with the description herein. Additionally, the operator may sever tissue captured between electrode surfaces (420, 440, 442) in accordance with the description herein. With the appropriate, non-uniform final gap distance (d1) created along the length of tissue grasping assembly (410), the tissue captured along the entire length of electrodes (420, 440, 442) may be suitably sealed/welded without damaging/crushing any portion of the grasped tissue.

Next, the operator may distally translate pin (350) such that upper jaw (484) pivots away from lower jaw (482), thereby removing the reactionary force imparted on electrode surfaces (440, 442) and upper jaw (484) from teeth (426, 428). Due to the resilient nature of electrodes (440, 442), the removal of the reactionary force allows electrode surfaces (440, 442) to return to their original shape as shown in FIGS. 8A-8B and FIG. 9A.

Since proximal teeth (424) are dimensioned to be housed within recess (446) of upper tissue grasping portion (414), in some instances, proximal teeth (424) may be omitted. In some instances, proximal teeth (424) may be electrically coupled with electrode surface (420).

In the current example, middle teeth (426) and distal teeth (428) together define a distal portion of gap distance (d1) while also preventing electrode surface (420) from accidentally contacting correspond surfaces (440, 442). However, this is merely optional. In instances where distal teeth (428) extend further from electrode surface (420) as compared to middle teeth (426), distal teeth (428) alone may be used to define gap distance (d1). In instances where middle teeth (426) extend further from electrode surface (420) as compared to distal teeth (428), middle teeth (426) alone may be used to define gap distance (d1).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body; and (c) an end effector configured to grasp tissue and transmit RF energy to the grasped tissue, wherein the end effector comprises: (i) a first jaw member comprising a first tissue grasping feature, and (ii) a second jaw member, wherein the second jaw member is pivotably coupled to the first jaw member between an open position, a partially closed position, and a closed position, wherein the second jaw member comprises: (A) a proximal taper comprising a proximal electrode surface terminating at a proximal end, (B) a distal taper comprising a distal electrode surface terminating at a distal end, and (C) a juncture interposed between the proximal electrode surface and the distal electrode surface, wherein the juncture is configured to be spaced further from the first tissue grasping feature compared to the proximal end and the distal end while the second jaw is in the partially closed position, wherein the proximal electrode surface and the distal electrode surface are configured to deform to define a gap with the first tissue grasping feature between the proximal end and the distal end while in the closed position.

Example 2

The apparatus of Example 1, wherein the first tissue grasping feature comprises an electrode surface and a distal pair of teeth electrically insulated from the electrode surface.

Example 3

The apparatus of Example 2, wherein the distal electrode surface is configured to contact the distal pair of teeth in the partially closed position and the fully closed position.

Example 4

The apparatus of Example 3, wherein the distal pair of teeth extend away from the electrode surface in order to define the gap distance.

Example 5

The apparatus of any one or more of Examples 1 through 4, wherein the juncture comprises a first thickness, wherein the distal end comprises a second thickness, wherein the first thickness is smaller than the second thickness.

Example 6

The apparatus of Example 5, wherein the proximal end comprises a third thickness, wherein the first thickness is smaller than the third thickness.

Example 7

The apparatus of any one or more of Examples 1 through 6, wherein the first tissue grasping feature comprises an electrode surface, a distal pair of teeth electrically insulated from the electrode surface, and a second pair of teeth.

Example 8

The apparatus of Example 7, wherein the second pair of teeth are proximal relative to the distal pair of teeth.

Example 9

The apparatus of Example 8, wherein the second pair of teeth are configured to contact the distal electrode surface in the closed position.

Example 10

The apparatus of Example 9, wherein the second pair of teeth are configured to be spaced away from the distal electrode surface in the partially closed position.

Example 11

The apparatus of any one or more of Examples 8 through 10, wherein either the proximal electrode surface or the distal electrode surface defines a recess, wherein the recess is dimensioned to house the second pair of teeth in the closed position.

Example 12

The apparatus of any one or more of Examples 1 through 11, wherein the body comprises a handle assembly.

Example 13

The apparatus of Example 12, wherein the handle assembly further comprises a jaw closure trigger, wherein the jaw closure trigger is configured to pivot the second jaw between the open position, the partially closed position, and the fully closed position.

Example 14

The apparatus of any one or more of Examples 12 through 13, wherein the handle assembly comprises an activation button configured to transmit RF energy to the proximal electrode surface and the distal electrode surface.

Example 15

The apparatus of any one or more of Examples 1 through 14, wherein the proximal electrode surface and the distal electrode surface are configured to deform to define a non-uniform gap with the first tissue grasping feature between the proximal end and the distal end while in the closed position.

Example 16

An apparatus comprising: (a) a body; and (b) an end effector located distally relative to the body, wherein the end effector is configured to grasp tissue and transmit RF energy to the grasped tissue, wherein the end effector comprises: (i) a first jaw member, and (ii) a second jaw member, wherein the second jaw member is pivotably coupled to the first jaw member between an open position, a partially closed position, and a closed position, wherein the second jaw member comprises a double tapered electrode surface comprising a proximal taper and a distal taper connected at a juncture, wherein the juncture is configured to be spaced further from the first tissue grasping feature compared to the proximal taper and the distal taper while the second jaw is in the partially closed position, wherein the proximal taper and the distal taper are configured to deform to define a gap with the first jaw member while in the closed position.

Example 17

The apparatus of Example 16, wherein the first jaw member comprises an electrode surface.

Example 18

The apparatus of Example 17, wherein the first jaw member comprises at least one tooth electrically insulated from the electrode surface of the first jaw member.

Example 19

The apparatus of Example 18, wherein the at least one tooth is configured to contact the distal taper while the second jaw is in the closed position.

Example 20

An apparatus comprising: (a) a body; (b) a shaft assembly extending distally from the body; and (c) an end effector configured to grasp tissue and transmit RF energy to the grasped tissue, wherein the end effector comprises: (i) a first jaw member, (ii) a second jaw member, wherein the second jaw member is pivotably coupled to the first jaw member between an open position, a partially closed position, and a closed position, and (iii) a tissue grasping assembly, comprising (A) a first tissue grasping feature associated with the first jaw member, and (B) a second tissue grasping feature associated with the second jaw member, wherein the second tissue grasping feature comprises a compliant electrode surface, wherein the compliant electrode surface is configured to form a double taper while the second jaw is in the open position and the partially closed position, wherein the compliant electrode surface is configured to deform to define a gap distance with the first tissue grasping feature while in the closed position.

IV. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein. For instance, the teachings herein may be readily combined with various teachings in U.S. Pat. No. 9,526,565, the disclosure of which is incorporated by reference herein; U.S. Pat. No. 9,492,224, the disclosure of which is incorporated by reference herein; and/or U.S. Pat. No. 10,292,758, the disclosure of which is incorporated by reference herein. Various suitable ways in which such teachings may be combined will be apparent to those of ordinary skill in the art.

It should also be understood that any of the devices described herein may be modified to include a motor or other electrically powered device to drive an otherwise manually moved component. Various examples of such modifications are described in U.S. Pat. No. 9,161,803, entitled "Motor Driven Electrosurgical Device with Mechanical and Electrical Feedback," issued Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410, 603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. No. 8,461,744, entitled "Rotating Transducer Mount for Ultrasonic Surgical Instruments," issued on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body; and
   (b) an end effector located distally relative to the body, wherein the end effector is configured to grasp tissue and transmit RF energy to the grasped tissue, wherein the end effector comprises:
      (i) a first jaw member comprising a first electrode surface and at least one tooth electrically insulated from the first electrode surface, and
      (ii) a second jaw member pivotally coupled to the first jaw member between an open position, a partially closed position, and a closed position, wherein the second jaw member comprises:
         (A) a proximal electrode surface,
         (B) a distal electrode surface configured to engage the at least one tooth of the first jaw member in the partially closed position and the closed position at an engagement location, and
         (C) a juncture interposed between the proximal electrode surface and the distal electrode surface, wherein the distal electrode surface continuously tapers from the juncture to the engagement location,
         wherein, while in the closed position, the distal electrode surface is configured to deform in response to a bending force generated by the at least one tooth engaging the engagement location of the distal electrode surface to define a gap with the first electrode surface.

2. The apparatus of claim 1, wherein the proximal electrode surface terminates at a proximal end, wherein the proximal electrode surface continuously tapers from the juncture to the proximal end.

3. The apparatus of claim 2, wherein the proximal electrode surface and the distal electrode surface cooperatively form a camber with the juncture.

4. The apparatus of claim 2, wherein the proximal electrode surface and the distal electrode surface are in electrical communication with each other.

5. The apparatus of claim 2, wherein the proximal electrode surface and the distal electrode surface are formed as a single piece of material.

6. The apparatus of claim 1, wherein the juncture extends linearly between a first lateral side and a second lateral side of the second jaw member.

7. The apparatus of claim 1, wherein the juncture extends perpendicular between a first lateral side and a second lateral side of the second jaw member.

8. The apparatus of claim 1, wherein the distal electrode surface comprises a planar profile and a rectangular perimeter.

9. The apparatus of claim 1, wherein distal electrode surface continuously tapers from the juncture to the engagement location via a change in thickness of the distal electrode surface.

10. The apparatus of claim 1, wherein the first electrode surface defines at least one pocket, wherein each tooth of the at least one tooth is housed within a respective pocket of the at least one pocket.

11. The apparatus of claim 1, further comprising a shaft interposed between the body and the end effector.

12. The apparatus of claim 1, wherein the body comprises a handle assembly.

13. An apparatus, comprising:
   (a) a body; and
   (b) an end effector located distally relative to the body, wherein the end effector is configured to grasp tissue and transmit RF energy to the grasped tissue, wherein the end effector comprises:
      (i) a first jaw member comprising a first electrode surface and at least one tooth electrically insulated from the first electrode surface, and
      (ii) a second jaw member pivotally coupled to the first jaw member between an open position, a partially closed position, and a closed position, wherein the second jaw member comprises:
         (A) a proximal electrode surface comprising a first longitudinally extending taper,
         (B) a distal electrode surface comprising a second longitudinally extending taper, wherein the distal electrode surface is configured to engage the at least one tooth of the first jaw member in the partially closed position and the closed position at an engagement location, and
         (C) a juncture interposed between the proximal electrode surface and the distal electrode surface,
         wherein the distal electrode surface continuously tapers in a direction toward the first electrode surface between the juncture and the engagement location,
         wherein, while in the closed position, the distal electrode surface is configured to deform in response to a bending force generated by the at least one tooth engaging the engagement location of the distal electrode surface to define a gap with the first electrode surface.

14. The apparatus of claim 13, wherein the first longitudinally extending taper and the second longitudinally extending taper extend from the juncture along a slightly arched profile.

15. The apparatus of claim 13, wherein the first longitudinally extending taper extends toward the juncture in a direction facing away from the first electrode surface while the second jaw is in the partially closed position.

16. The apparatus of claim 13, wherein the distal electrode surface and the proximal electrode surface are each formed of an elastically deformable material.

17. The apparatus of claim 13, further comprising a knife member.

18. The apparatus of claim 17, further comprising a knife trigger configured to actuate the knife member within the first jaw and the second jaw in the closed position.

19. An apparatus, comprising:
   (a) a body; and
   (b) an end effector located distally relative to the body, wherein the end effector is configured to grasp tissue and transmit RF energy to the grasped tissue, wherein the end effector comprises:

(i) a first jaw member comprising a first electrode surface and at least one tooth electrically insulated from the first electrode surface, and
(ii) a second jaw member pivotally coupled to the first jaw member between an open position, a partially closed position, and a closed position, wherein the second jaw member comprises:
(A) a proximal electrode surface,
(B) a distal electrode surface comprising a longitudinally extending taper, wherein the distal electrode surface is configured to engage the at least one tooth of the first jaw member in the partially closed position and the closed position at an engagement location, and
(C) a juncture interposed between the proximal electrode surface and the distal electrode surface,
wherein the distal electrode surface tapers between the juncture and the engagement location such that a first portion of the distal electrode surface adjacent to the engagement location is closer to the first electrode surface compared to a second portion of the distal electrode surface adjacent to the juncture, while the second jaw is in the partially closed position,
wherein, while in the closed position, the distal electrode surface is configured to deform in response to a bending force generated by the at least one tooth engaging the engagement location of the distal electrode surface to define a gap with the first electrode surface.

20. The apparatus of claim 19, wherein the proximal electrode surface and the distal electrode surface form a double taper.

* * * * *